United States Patent [19]

Allison et al.

[11] Patent Number: 4,899,004

[45] Date of Patent: Feb. 6, 1990

[54] PROCESS FOR PRODUCING TRIMETHYLBENZENE

[75] Inventors: Joe D. Allison; Richard M. Tillman, both of Ponca City, Okla.

[73] Assignee: Conoco Inc., Ponca City, Okla.

[21] Appl. No.: 242,110

[22] Filed: Sep. 9, 1988

[51] Int. Cl.$^4$ .................... C07C 2/00; C07C 2/08
[52] U.S. Cl. .................... 585/321; 585/322; 585/638; 585/639; 585/733; 585/415; 585/416; 585/417
[58] Field of Search ............ 585/321, 322, 638, 639, 585/733, 415, 416, 417

[56] References Cited

U.S. PATENT DOCUMENTS

| | | | |
|---|---|---|---|
| 889,993 | 2/1862 | Huebel et al. | 73/795 |
| 3,126,424 | 3/1964 | Mueller et al. | 585/416 |
| 3,204,008 | 8/1965 | Scheller et al. | 585/413 |
| 3,718,704 | 2/1973 | Chapman et al. | 585/467 |
| 3,781,907 | 2/1957 | Schmerling | 585/321 |
| 4,009,219 | 2/1977 | Tamers | 585/416 |
| 4,058,450 | 11/1977 | LePage et al. | 585/322 |
| 4,172,810 | 10/1979 | Mitchell et al. | 585/417 |
| 4,205,194 | 5/1980 | Mitchell et al. | 585/419 |
| 4,239,658 | 12/1980 | Mitchell et al. | 585/417 |
| 4,499,325 | 2/1985 | Klotz et al. | 585/322 |

FOREIGN PATENT DOCUMENTS 595668 4/1960 Canada .

OTHER PUBLICATIONS

Hydrolysis of Magnesium Sesquicarbide $Mg_2C_3$; Bohumil Hajek, Pavel Karen and Vlastimil Brozek; Collection Czechoslov, Chem. Commun. (vol. 45) (1980) pp. 3408-3416.

Thermal Decomposition of Magnesium Sesquicarbide; Bohumil Hajek, Pavel Karen and Vlastimil Brozek; Collection Czechoslovak, Commun. (vol. 48) (1983) pp. 1963-1968.

Synthesis and Thermal Decomposition of Magnesium Dicarbide; Bohumil Hajek, Pavel Karen and Vlastimil Brozek; Collection Czechoslovak, Commun. (vol. 48) (1983) pp. 1969-1976.

Primary Examiner—Patrick P. Garvin
Assistant Examiner—E. D. Irzinski
Attorney, Agent, or Firm—Cleveland R. Williams

[57] ABSTRACT

Trimethylbenzene is selectively prepared by contacting a $C_1$ to $C_4$ alkane with magnesium under reaction conditions to produce a reaction product. The reaction product thus produced, is contacted with water or a lower alcohol to promote a protonolysis reaction. The reaction mixture or a fraction thereof from the protonolysis reaction is contacted with a metal containing Y zeolite catalyst under reaction conditions to produce trimethylbenzene.

22 Claims, No Drawings

PROCESS FOR PRODUCING TRIMETHYLBENZENE

BACKGROUND OF THE INVENTION

1. Field of the Invention

The present invention resides in a process for selectively producing trimethylbenzene by gas phase reaction of a $C_1$ to $C_4$ alkane with magnesium to produce a reaction product. The reaction product is subjected to a protonolysis reaction with either water or an alcohol to produce a reaction mixture. Finally, the reaction mixture or a fraction thereof, thus produced, is contacted with a metal containing Y zeolite catalyst under reaction conditions.

Trimethylbenzene occurs naturally in petroleum reformate as its three isomers, namely, pseudocumene (1,2,4 trimethylbenzene), mesitylene (1,3,5 trimethylbenzene) and hemimellitene (1,2,3 trimethylbenzene), but only pseudocumene can be isolated from the petroleum reformate in high purity with a reasonable yield due to distillation limitations. Additionally, trimethylbenzene is produced commercially in the petroleum industry by catalytic reforming and catalytic cracking operations usually involving straight run naphthas.

More recently, trimethylbenzene has been produced in the United States by the Koch Company, utilizing what is commonly known as the Koch Process. This process is based on alkylation, isomerization and disproportionation reactions which are conducted in the presence of a Friedel-Crafts Catalyst. For example, benzene is reacted with an alkylhalide or an alkyl alcohol in the presence of aluminum chloride to prepare an alkylated benzene.

Generally, trimethylbenzene has previously been used as a blending stock for gasoline and aviation fuel because of its unique octane enhancing property. Trimethylbenzene may be converted to sterically hindered phenols which are utilized as non-coloring stabilizers (antioxidants) for plastics, adhesives, rubber and waxes. It should be noted that the isomeric trimethylbenzenes are valuable intermediates for the production of many organic compounds including acids, ketones and the like. In addition, trimethylbenzene is useful as a dye intermediate (e.g., as 2,4,6 trimethylanaline) and as a perfume additive.

2. Description of the Prior Art

Processes and catalysts for the production of substituted aromatic compounds from relatively low molecular weight hydrocarbons are known and are currently practiced commercially.

For example, U.S. Pat. No. 3,204,008, issued August 31, 1965, relates to a process for preparing aromatic compounds from acetylenically unsaturated compounds using a catalyst consisting of mixtures of the halides of tantalum, or of the halides or oxyhalides of niobium or of mixtures thereof.

U.S. Pat. No. 4,009,219, issued February 22, 1977, relates to a method for producing benzene wherein non-hydrocarbon carbonaceous raw materials are reacted with an alkali metal or an alkaline earth metal to produce a metallic carbide. The metallic carbide is hydrolyzed to produce acetylene and the acetylene is cyclized to benzene using a chromium VI or vanadium VI activated silica-aluminum catalyst.

U.S. Pat. No. 4,172,810, issued October 30, 1979, discloses catalyst compositions which are described as suitable for the conversion and oligomerization of hydrocarbons, in particular, methane to produce ethylene or benzene. The catalyst consists of an inorganic-oxide support, preferably alumina, composited with the Group IB, IIA, VIB or VII metals and barium.

U.S. Pat. No. 4,205,194, issued May 27, 1980, relates to a process for the conversion and oligomerization of hydrocarbons, notably methane to produce ethylene or benzene. The process utilizes a catalyst consisting of an inorganic-oxide support, for example, alumina, composited with the Group IB, IIA, VIB or VIII metals.

Canadian Pat. No. 595,668, issued April 5, 1960, discloses a process for the polymerization of acetylenic compounds, wherein the acetylenic compound is brought into contact with a reaction medium consisting of an organo-compound reacted with at least one non-transition metal of Groups I, II and III, and a compound of a transitional metal.

PUBLICATIONS

*Hydrolysis Of Magnesium Sesquicarbide*, by Bohumil Hajek, Pavel Karen and Vlastimil Brozek; Collection Czechoslovak Chem. Commun., Vol. 45, Pages 3408 to 3416 (1980). This publication relates to a method for producing magnesium sesquicarbide by reacting magnesium metal with n-pentane. Magnesium sesquicarbide is converted to propyne and propadiene by hydrolysis with water.

*Thermal Decomposition Of Magnesium Sesquicarbide*, by Bohumil Hajek, Pavel Karen and Vlastimil Brozek; Collection Czechoslovak Chem. Commun., Vol. 48, Pages 1963 to 1968 (1983). This article discloses a method for interpreting the formation of magnesium sesquicarbide from magnesium and hydrocarbons as a reaction of radicals with magnesium vapors.

It should be noted that the above patents and publications, either singularly or collectively, fail to disclose a process, including catalysts, which are suitable for selectively preparing trimethylbenzene in high yields form $C_1$ to $C_4$ alkanes and mixtures thereof. As can readily be determined from the above, there is an ongoing search for new and more efficient processes and catalysts for producing alkylated aromatics from lower molecular weight hydrocarbons.

SUMMARY OF THE INVENTION

The present invention resides in a process for selectively producing trimethylbenzene from lower molecular weight hydrocarbons which comprises, (a) contacting a $C_1$ to $C_4$ alkane and mixtures thereof with metallic magnesium under reaction conditions, (b) contacting the reaction product or a fraction thereof produced in (a) with water or an alcohol under reaction conditions, and (c) contacting the reaction mixture or a fraction thereof produced in (b) with an ion-exchanged, Y zeolite catalyst composited with a metal selected from the Group VIB and VIII metals and mixtures thereof.

DETAILED DESCRIPTION OF THE INVENTION

A three-step process is provided for the selective preparation of trimethylbenzene, wherein $C_1$ to $C_4$ alkanes are contacted with metallic magnesium under reaction conditions to produce a reaction product. The reaction product or a fraction thereof thus produced is contacted with water or a lower alcohol under sufficient reaction conditions to promote a hydrolysis or an alcoholysis reaction. Finally, the reaction mixture produced in the hydrolysis or alcoholysis reaction is contacted with a Y zeolite catalyst which has been composited with a Group VIB or VIII metal of the Periodic Table or mixtures thereof, to promote a cyclotrimerization reaction.

Hydrocarbon feedstocks suitable for use in the trimethylbenzene process herein include the $C_1$ to $C_4$ alkanes. The $C_1$ to $C_4$ alkanes may be introduced into the reaction medium either individually or as a mixture. It should be noted however that the reaction with magnesium proceeds at a faster rate as the number of carbon atoms increase in the alkane chain. The $C_1$ to $C_4$ alkanes are selected from the group consisting of methane, ethane, propane, and butane and mixtures thereof. The preferred alkane is methane, primarily due to the widespread availability of this compound.

Methane is the principal component of natural gas which is produced in substantial quantities in oil and gas fields, often in difficult terrain and/or in remote locations. If the field is too remote for the gas (including methane) to be recovered on an economical basis, the gas is routinely flared off or shut in the well. Thus, the use of methane to produce higher hydrocarbons offers an excellent opportunity to utilize a valuable natural resource which is sometimes wasted because it cannot be commercially recovered. Other sources for methane include refineries and chemical plants which produce methane as a by-product with other more valuable hydrocarbons or as an off gas.

The $C_1$ to $C_4$ alkane is conveniently contacted with magnesium to promote the production of magnesium sesquicarbide. The magnesium utilized is preferably a technical grade which is from about 98 to about 99 percent pure. However, less pure commercial grades of magnesium may be used with substantially similar results in the production of magnesium sesquicarbide. The $C_1$ to $C_4$ alkane and magnesium are contacted at a reaction temperature of from about 450° C. to about 650° C., especially from about 500° C. to about 640° C., preferably from about 620° C. to about 630° C.; a pressure of from about atmospheric pressure to about 100 psig, preferably from about atmospheric pressure to about 25 psig, most preferably from about atmospheric pressure to about 5 psig; and a contact time of from about 0.01 to about 10, especially from about 0.05 to about 5, preferably from about 0.1 to about 2 ml of alkane per minute per gram of magnesium. It should be noted that the reaction product produced herein predominates in magnesium sesquicarbide, however, minor amounts of magnesium carbide may be produced in the reaction.

The reaction product or a fraction thereof, thus produced, is contacted with either water to promote a hydrolysis reaction or a lower aliphatic alcohol to promote an alcoholysis reaction. It should be noted that the hydrolysis and alcoholysis reactions herein are jointly referred to as a protonolysis reaction. Preferably the water or alcohol is introduced into the reaction medium in the form of a water or alcohol saturated gas. The type gas used to introduce the water or alcohol into the reaction medium is not critical so long as the gas is inert. A gas suitable for use herein as a water or alcohol carrier is helium, but other inert gases may be used.

Lower aliphatic alcohols which are suitable for use include methanol, ethanol, propanol, isopropanol and the like. The reaction product and either water or alcohol are contacted at a reaction temperature of from about 20° C. to about 300° C., preferably from about 50° C. to about 250° C., most preferably from about 180° C. to about 200° C.; a pressure of from about atmospheric pressure to about 100 psig, especially from about atmospheric pressure to about 25 psig, preferably from about atmospheric pressure to about 5 psig; and a contact time of from about 0.01 to about 10, normally from about 0.5 to about 5, especially from about 1 to about 2 ml of water or alcohol saturated gas per gram of reaction product.

Generally, the hydrolysis or alcoholysis of magnesium sesquicarbide will produce a reaction mixture which consists of methylacetylene, allene, propylene, propane, magnesium hydroxide and minor amounts of unreacted magnesium sesquicarbide and $C_1$ to $C_4$ alkane. The compounds produced in the reaction which are suitable for use in the cyclotrimerization reaction, however, are methylacetylene, allene and propylene. It should be noted that the entire reaction mixture may be sujected to a cyclotrimerization reaction to produce trimethylbenzene. The preferred compounds for using in a cyclotrimerization reaction consists of a fraction of the reaction mixture, for example methylacetylene and allene. Methylacetylene is especially preferred as the starting compound in the production of trimethylbenzene.

The cyclotrimerization catalyst preferably comprises an inorganic refractory oxide support or matrix composited with a metal or mixture of metals selected from the Group VIB and VIII metals of the Periodic Table. The preferred inorganic refractory oxide is an aluminosilicate compound.

The inorganic refractory oxides suitable for use herein preferably comprise a metal containing Y zeolite. The Y zeolites belong to the broad class of aluminosilicate molecular sieves characterized by, as the fundamental unit, a tetrahedral complex consisting of a small complex, for example, a silicon ion ($Si^{+4}$) in tetrahedral coordination with four oxygen atoms. The aluminum ion ($Al^{+3}$) commonly coordinates tetrahedrally, as well as octahedrally, with oxygen in zeolite formations. This coordinating ability of the aluminum ion has a profound effect on zeolite structures and their final composition. In general, the complexity of zeolite structures occurs because of the various ways in which the tetrahedra groups may link by the common sharing of oxygen ions to form polynuclear complexes.

Substitution of aluminum for a silicon ion produces a deficiency in electrical charge that must be neutralized locally by an additional positive ion within the matrix of the zeolite structure. Aluminosilicates having different structures result from differences in the manner in which the tetrahedra may link in space in either one, two or three dimensions, and, additionally, from the types of other ions that substitute within the zeolite matrix; for example, the Group VIB or VIII metals of the Periodic Table as disclosed by the E. H. Sargent & Co.

The cyclotrimerization catalysts herein comprise a Group VIB or VIII metal Y zeolite or mixtures thereof characterized by an aluminosilicate framework consisting of a diamond-like array of truncated octahedra, B-cages, linked tetrahedrally through double 6-rings and containing 8 cavities of approximately 13 Angstroms in diameter in each unit cell. The linkage between adjoining truncated octahedra is a double 6-ring or hexagonal prism containing approximately 12 (Si, Al) $O_2$ tetrahedra.

The unit cells are cubic with a large cell dimension of nearly 25 Angstroms and contain approximately 192 (Si, Al) O₄ tetrahedra. The chemical composition of aluminosilicate, zeolite Y is related to the synthesis method used to prepare the zeolite. Differences in zeolite Y are related to the zeolite cation composition and distribution, the Si/Al ratio and possibly the Si to Al ordering in tetrahedral sites. The aluminum ions in the unit cell of zeolite Y vary from about 48 to about 76. The framework density of zeolite Y is from about 1.25 to about 1.29 g/cc, expressed as the number of structural framework tetrahedra per unit volume of 1000 Angstroms³.

In their sodium form, the Y zeolites suitable for use herein correspond to the general formula:

$$0.9 \pm 0.2 NaO: Al_2O_3: nSiO_2: X H_2O$$

wherein n is an integer of from about 3 to about 6 and X is an integer of from about 0 to about 9.

The Y zeolites herein are preferably ion exchanged with a metal selected from the Group VIB and VIII metals and mixtures thereof as disclosed by the Periodic Table. A Periodic Table marketed by the Sargent-Welch Scientific Company, Skokie, Illinois, may be consulted to determine the metals included in Groups VIB and VIII. Group VIB metals particularly suitable for use herein include chromium, molybdenum or tungsten and mixtures thereof. The preferred Group VIB metal herein is chromium. The Group VIII metals herein are preferably selected from the group consisting of iron, cobalt, nickel, ruthenium, rhodium, palladium, osmium, iridium, or platinum and mixtures thereof. The preferred metals are nickel, or cobalt and mixtures thereof. The metals disclosed herein may be in salt form, acid form or introduced into the Y zeolite as an oxide. Especially desirable salt forms of the metals herein include the metal chlorides and metal nitrates.

The metals are conveniently deposited on the Y zeolite by the incipient wetness technique. For example, an aqueous solution of the metal chloride or metal nitrate is formed and the Y zeolite is immersed in the solution. The metal impregnated Y zeolite is then dried under vacuum at a temperature of from about 250° C. to about 500° C. for from about one hour to about 5 hours.

Normally, the Group VIB or VIII metals comprise from about 1 weight percent to about 30 weight percent, preferably from about 3 weight percent to about 10 weight percent, especially from about 5 weight percent to about 8 weight percent, of the Y zeolite. When more than one metal is incorporated into the catalyst, they may be mixed in any molar ratio, so long as the weight percentages remain in the above-described ranges.

The final cyclotrimerization catalyst is characterized as having an average pore diameter of from about 60 Angstroms to about 400 Angstroms, preferably from about 80 Angstroms to about 340 Angstroms; a surface area ranging from about 50 M²/g to about 800 M²/g, especially from about 300 M²/g to about 600 M²/g; a pore volume of from about 0.2 cc/g to about 0.9 cc/g, preferably from about 0.5 cc/g to about 0.8 cc/g; and a compacted bulk density of from about 0.45 to about 0.85 especially from about 0.50 to about 0.65.

Hydrocarbon feedstocks suitable for use in the cyclotrimerization reaction herein, include the reaction mixture or a fraction thereof from the protonolysis reaction. The preferred hydrocarbon feedstock is methylacetylene, allene and propylene and mixtures thereof; especially methylacetylene.

The cyclotrimerization reaction is conveniently carried out by contacting either the reaction mixture or fraction thereof from the protonolysis reaction with the Y zeolite catalyst containing either a Group VIB metal or a Group VIII metal or mixture thereof, under reaction conditions. The reaction mixture or fraction thereof and cyclotrimerization catalyst are contacted at a reaction temperature between about 50° C. to about 250° C., preferably between about 80° C. to about 200° C., most preferably from about 100° C. to about 185° C.; a pressure of from about atmospheric pressure to about 50 psig, preferably from about atmospheric pressure to about 15 psig, especially from about atmospheric pressure to about 5 psig; and a contact time of from about 0.01 to about 10, preferably from about 0.05 to about 5, most preferably from about 0.1 to about 2 ml of reaction mixture or fraction thereof per minute, per gram of cyclotrimerization catalyst. It should be noted that the yield of trimethylbenzene herein is approximately 98 percent with a selectivity of approximately 95 percent. The isomers of trimethylbenzene are produced in the following amounts: 1,2,4-trimethylbenzene (approximately 66 percent), 1,3,5-trimethylbenzene (approximately 33 percent), and 1,2,3-trimethylbenzene (less than 1 percent).

DESCRIPTION OF THE PREFERRED EMBODIMENTS

The following examples serve to further illustrate to one skilled in the art the best mode of how to practice this invention and are not intended to be construed as limiting thereof.

EXAMPLE I

Catalyst A

A cyclotrimerization catalyst was prepared by impregnating a zeolite Y type support, via the incipient wetness technique, with an aqueous solution of nickel chloride. The nickel chloride solution was added to the zeolite Y support in an amount calculated to deposit 7.8 weight percent of nickel on the support. The nickel impregnated zeolite Y support was dried under vacuum at 350° C. for two hours.

EXAMPLE II

Catalyst B

A cyclotrimerization catalyst was prepared by impregnating a zeolite Y type support, using the incipient wetness technique, with an aqueous solution of chromium nitrate. The chromium impregnated zeolite Y support was dried under vacuum at 350° C. for two hours. The catalyst contained approximately 7 weight percent of chromium.

EXAMPLE III

Methane gas was cyclotrimerized to trimethylbenzene by introducing into a first pressure reactor 50 grams of magnesium. The reactor was a stainless steel downhole tubular reactor having a length of 24 inches, an inside diameter of 0.43 inches, and an outside diameter of 0.5 inches, equipped with heating tapes controlled by a Cole-Palmer Digi-Sens Temperature Controller. The first reactor contained Swagelok fittings on each end, connected to 0.125 inch nylon tubing. The flow of methane into the top end of the reactor was controlled by Whitney needle valves connected to Sierra Model 802 mass flow meters.

The first reactor was connected in series to a second stainless steel downhole tubular reactor with the 0.125 inch nylon tubing extending from the bottom end of the first reactor to the top end of the second reactor. The second reactor had the same physical dimensions as the first reactor and contained 23 grams of catalyst A.

Methane gas was introduced into the first reactor at a rate of 0.1 ml per minute per gram of magnesium for three hours at a temperature of 620° C. and at atmospheric pressure. The first reactor was cooled to 200° C., at atmospheric pressure, and reacted with a stream of wet (water contacting) helium flowing at a rate of 1.6 ml per minute per gram of magnesium for 2 hours.

The resulting hydrocarbon mixture of methylacetylene, allene and propylene was dried by a cold trap held by −10° C. and introduced into the second reactor containing a fixed bed of 23 grams of catalyst A at a temperature of 180° C., at atmospheric pressure and a flow rate of 0.2 ml per minute of hydrocarbon mixture per gram of catalyst A for 2 hours.

Analysis of the reaction mixture indicated that the yield of trimethylbenzene was 27 percent from methane with a selectivity of 95 percent.

EXAMPLE IV

The procedure of Example III was followed to produce trimethylbenzene with the following exceptions:

Ethane gas was substituted for the methane and the flow rate for the ethane gas into the first reactor was 0.1 ml per minute per gram of magnesium for 3 hours. The yield of trimethylbenzene was 32 percent from ethane with a selectivity of 95 percent.

EXAMPLE V

Trimethylbenzene was produced by following the procedure of Example III with the following exceptions:

Butane was substituted for the methane and the flow rate for the butane into the first reactor was 0.1 ml per minute per gram of magnesium for 3 hours. The yield of trimethylbenzene was 37 percent from butane with a selectivity of 95 percent.

As can readily be determined from the above Examples, the process herein selectively produces trimethylbenzene in high yields. Obviously, many modifications and variations of the invention, as hereinbefore set forth, may be made without departing from the spirit and scope thereof, and therefore only such limitations should be imposed as are indicated in the appended claims.

We claim:

1. A process for selectively producing trimethylbenzene which comprises:
    (a) contacting a $C_1$ to $C_4$ alkane with magnesium at a temperature of from about 450° C. to about 650° C., a pressure of from about atmospheric pressure to about 100 psig and a contact time of from about 0.01 to about 10 ml of alkane per minute per gram of magnesium;
    (b) contacting the reaction product or a fraction thereof produced in step (a) with water or alcohol to promote a protonolysis reaction; and
    (c) contacting the reaction mixture or fraction thereof produced in step (b) with a Y zeolite catalyst containing a metal selected from a Group VIB metal or a Group VIII metal and mixtures thereof at a temperature of from about 50° C. to about 250° C., a pressure of from about atmospheric pressure to about 50 psig and a contact time of from 0.01 to about 10 ml of reaction mixture or fraction thereof per minute per gram of Y zeolite catalyst.

2. The process according to claim 1 wherein the $C_1$ to $C_4$ alkane is a member selected from the group consisting of methane, propane, ethane, and butane and mixtures thereof.

3. The process according to claim 1 wherein the reaction product of step (a) comprises magnesium sesquicarbide and magnesium carbide and mixtures thereof.

4. The process according to claim 1 wherein the reaction conditions of the protonolysis reaction comprise a temperature of from 20° C. to about 300° C., a pressure of from about atmospheric pressure to about 100 psig and a contact time of from about 0.01 to about 10 ml of water or alcohol as a saturated gas per minute per gram of reaction product or fraction thereof.

5. The process according to claim 1 wherein the reaction mixture in step (b) comprises methylacetylene, allene, propane and propylene.

6. The process according to claim 1 wherein the Group VIB metal is a member selected from the group consisting of chromium, molybdenum and tungsten and mixtures thereof.

7. The process according to claim 1 wherein the Group VIII metal is a member selected from the group consisting of iron, cobalt, nickel, ruthenium, rhodium, palladium, osmium, iridium, and platinum and mixtures thereof.

8. The process according to claim 1 wherein the Group VIB or VIII metal comprises from about 1 weight percent to about 30 weight percent of the zeolite Y catalyst.

9. A process for selectively producing trimethylbenzene which comprises:
    (a) contacting a $C_1$ to $C_4$ alkane with magnesium at a temperature of from about 500° C. to about 640° C., a pressure of from about atmospheric pressure to about 25 psig, and a contact time of from about 0.05 to about 5 ml of alkane per minute per gram of magnesium;
    (b) contacting the reaction product or a fraction thereof of step (a) with water or alcohol at a temperature of from about 50° C. to about 250° C., a pressure of from about atmospheric pressure to about 25 psig and a contact time of from about 0.5 to about 5 ml of water or alcohol as a saturated gas per minute per gram of reaction product or fraction thereof; and
    (c) contacting the reaction mixture or fraction thereof of step (b) with a Y zeolite catalyst containing a metal selected from a Group VIB metal or a Group VIII metal and mixtures thereof at a temperature of from about 80° C. to about 200° C., a pressure of from about atmospheric pressure to about 15 psig and a contact time of from about 0.05 to about 5 ml of reaction mixture or fraction thereof per minute per gram of Y zeolite catalyst.

10. The process according to claim 9 wherein the $C_1$ to $C_4$ alkane is a member selected from the group consisting of methane, ethane, propane and butane and mixtures thereof.

11. The process according to claim 9 wherein the reaction product of step (a) comprises magnesium sesquicarbide and magnesium carbide and mixtures thereof.

12. The process according to claim 9 wherein the reaction product of step (b) comprises methylacetylene, allene, propane and propylene.

13. The process according to claim 9 wherein the Group VIB metal is a member selected from the group consisting of chromium, molybdenum and tungsten and mixtures thereof.

14. The process according to claim 9 wherein the Group VIII metal is a member selected from the group consisting of iron, cobalt, nickel, ruthenium, rhodium, palladium, osmium, iridium, and platinum and mixtures thereof.

15. The process according to claim 9 wherein the Group VIB or Group VIII metal comprises from about 3 weight percent to about 10 weight percent of the zeolite Y catalyst.

16. A process for selectively producing trimethylbenzene which comprises:

(a) contacting methane with magnesium at a temperature of from about 500° C. to about 640° C., a pressure of from about atmospheric pressure to about 25 psig, and a contact time of from about 0.05 to about 5 ml of methane per minute per gram of magnesium;

(b) contacting the reaction product or fraction thereof of step (a) with water or alcohol at a temperature of from about 50° C. to about 250° C., a pressure of from about atmospheric pressure to about 25 psig and a contact time of from about 0.5 to about 5 ml of water or alcohol as a saturated gas per minute per gram of reaction product or fraction thereof; and (c) contacting the reaction mixture or fraction thereof of step (b) with a Y zeolite catalyst containing a metal selected from a Group VIB metal or Group VIII metal and mixtures thereof at a temperature of from about 80° C. to about 200° C., a pressure of from about atmospheric pressure to about 15 psig and a contact time of from about 0.05 to about 5 ml of reaction mixture or fraction thereof per gram of Y zeolite catalyst.

17. The process according to claim 16 wherein the reaction product in step (a) comprises magnesium sesquicarbide and magnesium carbide and mixtures thereof.

18. The process according to claim 16 wherein the reaction mixture or fraction thereof in step (b) comprises methylacetylene, allene, propane and propylene.

19. The process according to claim 18 wherein the reaction mixture or fraction thereof comprises methylacetylene.

20. The process according to claim 16 wherein the Group VIB metal is a member selected from the group consisting of chromium, molybdenum and tungsten and mixtures thereof.

21. The process according to claim 16 wherein the Group VIII metal of the zeolite Y catalyst is a member selected from the group consisting of iron, cobalt, nickel, ruthenium, rhodium, palladium, osmium, iridium and platinum and mixtures thereof.

22. The process according to claim 16 wherein the Group VIB or Group VIII metal comprises from about 3 weight percent to about 10 weight percent of the zeolite Y catalyst.

* * * * *